ALSTROEMERIA HYBRID (YELLOW TIGER)

Filed April 9, 1971 2 Sheets-Sheet 1

INVENTOR.
MAURITS C. VAN STAAVEREN

BY Rummler & Snow
ATTYS.

ALSTROEMERIA HYBRID (YELLOW TIGER)

Filed April 9, 1971 2 Sheets-Sheet 2

United States Patent Office

Plant Pat. 3,281
Patented Jan. 2, 1973

3,281

ALSTROEMERIA HYBRID (YELLOW TIGER)

Maurits C. van Staaveren, 30 Hornweg,
Aalsmeer, Netherlands

Filed Apr. 9, 1971, Ser. No. 132,921
Int. Cl. A01h *5/00*
U.S. Cl. Plt.—68 1 Claim

ABSTRACT OF THE DISCLOSURE

A new variety of alstroemeria plant characterized by its novel color, the abundance of its annual crop of flower stalks, the profuse production of blossoms on each flower stalk, and the very long lasting quality of the blooming plant as a cut flower.

BACKGROUND OF THE INVENTION

My new variety of hybrid alstroemeria plant originated as a sport of the alstroemeria hybrid "Orchid" and was discovered by me in 1968 among greenhouse grown plants at Aalsmeer, Holland, the parent plant having been Roentgen radiated at the I.T.A.L. Institute at Wageningen, Holland. The unusual and pleasing color of this sport caused it to be selected for propagation and trial and asexual reproduction of the new plant through successive generations at Aalsmeer, Holland, showed the new plant to have a vigorous upright growth habit, a prolific production of blooms that are long lasting as cut flowers as well as on the plant, and blossoms that are not affected, either in color, texture or appearance, by wet or hot weather. Extensive reproduction of this new plant, by dividing the rootstock, has demonstrated that its novel and distinguishing characteristics are fixed and hold true from generation to generation.

Propagation of my new variety of alstroemeria plant is now being done on a commercial scale at Aalsmeer, Holland, and the following description is based upon observations made during August 1970.

DESCRIPTION OF THE DRAWING

The new variety of alstroemeria plant is illustrated by the accompanying photographic drawing which shows the color characteristics of the blossoms as nearly true as it is reasonably possible to obtain by conventional photographic procedures, and in which.

DESCRIPTION OF THE PLANT

The following is a detailed description of my new variety of astroemaria plant with the color designations according to the R.H.S. Colour Chart of the Royal Horticultural Society of London, England.

*The plant*

Origin: Sport.
Parentage: Alstroemeria hybrid "Orchid" (unpatented).
Form: Herb. Tall and slender flower stalk with flower bearing branches in umbel arrangement at its top.
Height: 1.5 to 2.0 meters at maturity.
Growth: Vigorous and upright.
Rootstock: Tuberous. Tubers grow about 15 cm. per year and each bears 40 to 50 buds from which flower stalks grow, in different stages of development, during the course of a year.

Figure 1:
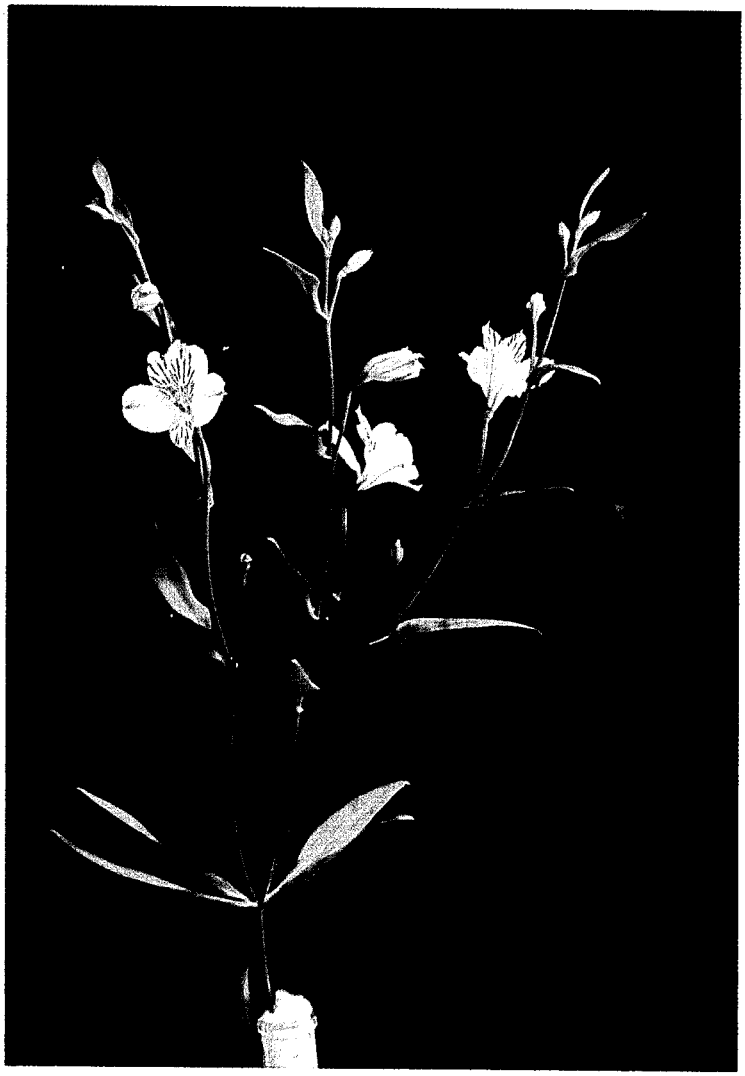
FIG. 1 is a view of the branching portion of a typical flower stalk of the new plant showing bud distribution and an open flower on each branch.

Branching: 3 to 7 (average 5) flower bearing branches on each flower stalk. Each branch is 30 to 40 cm. long and bears 5 to 7 (average 6) buds spaced 3 to 9 cm. apart along the branch stem. (See FIG. 1.)

Foliage—Leaves:
- *Quantity.*—About 20 to 30 leaves spaced along the flower stalk stem. At branching umbel a circle of leaves is formed, one leaf for each branch.
- *Shape of leaf.*—Long and narrow, generally linear with acuminate tip, curled at about 1.5 cm. from stem to turn the morphological underside upwardly.
- *Size of leaf.*—14 to 15 cm. long x 3.0 to 3.5 cm. wide.
- *Texture.*—Soft. Appearance: Shiny.
- *Color.*—Upper side—Yellow-Green 146A. Under side—Greyed-Green 191A.

*The bud*

Figure 2:
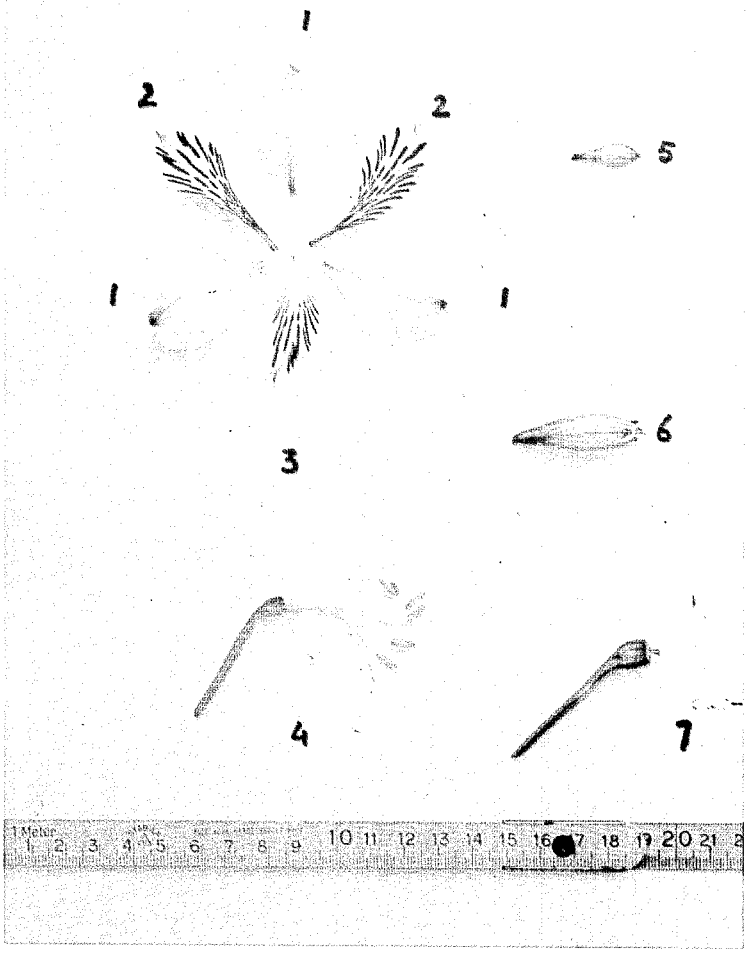
FIG. 2 shows the petals and reproductive organs of a single flower, young and mature buds, and a specimen of the fruit.

Form:
- *Young bud.*—12 days before opening—pear shaped, #5 in FIG. 2.
- *Mature bud.*—1 or 2 days before opening—long and pointed, #6 in FIG. 2.

Size: Just before opening—2.8 cm. long x 1 cm. in diameter.

Color:
- *Upper side.*—mainly Red-Purple 61B with veins of Green 141C.
- *Under side.*—mainly Green 141C with veins of Red-Purple 61B.

*The flower*

Blooming habit: Recurrent, two times a year, from March through June and from mid-August to end of October under Dutch climatological conditions. The flowering in the Fall season is less abundant than in Spring.

Figure 3:
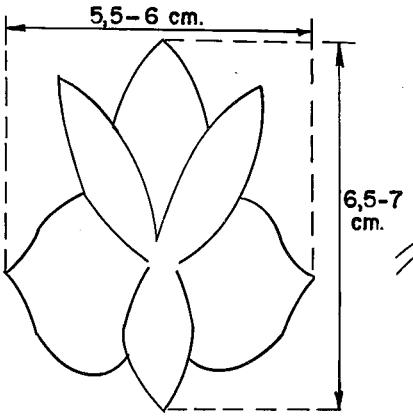
FIG. 3 is a sketch showing the front view arrangement of the flower petals.
Figure 4:
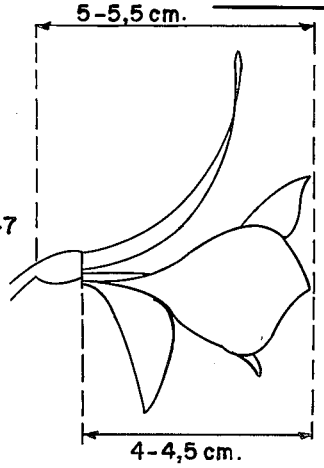
FIG. 4 is a sketch showing the side view arrangement of the same.

Size: Medium, 5 to 5.5 cm. long x 5.5 to 7 cm. diameter or spread of petals in face view. See FIGS. 3 and 4.

Borne: Singly, with 5 to 7 buds, spaced 3 to 9 cm. apart, appearing on each branch and with the buds flowering individually, in succession, about 3 days apart.

Shape: Generally funnel-like.

Petalage: 6 in number arranged in two concentric circles of 3 petals.
- *Form.*—Outer petals, #1 in FIG. 2, generally obovate with entire margin. Each of the lower pair has a nectary-like base end and a cuspidate apex. Inner petals—upper pair, #2 in FIG. 2, generally spatulate with entire margin, muchonate tip and long nectary at base. Lower petal, #3 in FIG. 2, generally obovate with mucronate tip.
- *Color.*—Outer petals, mainly Yellow 13B, with tip end White 155A ending with mucron slightly colored Red-Purple 60D. Petals have veins of Green 141C. Inner petals, nectary bearing petals #2 in FIG. 2, mainly Yellow-Orange 14A, with White 155A tip end and base and having lengthwise stripes of Greyed-Orange 166A, 0.4 to 1.2 cm. long and 0.1 cm. wide. Lower petal, #3 in FIG. 2, mainly Yellow-Orange 14A, with tip end and base of White 155A, and with stripes of Greyed-Orange 166A 0.4 to 1.4 cm. long and 0.1 cm. wide.
- *Texture.*—Soft. Appearance.—velvety.

Effect of weather: Color, texture, and appearance are not affected by wet or hot weather.

Lasting quality:
- *On plant.*—10 days for each flower.
- *As cut flower.*—7 days for each flower and up to about 3 weeks for the umbel of flowering branches.

*Reproductive organs*

Stamens (#4 in FIG. 2):

*Anthers.*—6 in number, 0.7 cm. in length, arranged one opposite to each petal, and of Yellow-Green 153B color.

*Filaments.*—3.5 to 4 cm. long and of White 155B color.

Pollen: Color—Yellow-Orange 14B.

Pistil: One only, 3.0 cm. long. Color—White 155B with a dash of Red-Purple 60D in the middle.

Stigma: Color—Yellow-Orange 14B, 3 in number.

*The fruit*

Generally round in shape, #7 in FIG. 2, and of capsular form with three internal compartments each containing two rows of ovaries attached to the central standing placenta. There are no seeds produced and the plant is infertile.

My new variety of alstroemeria plant differs materially from all other cultivated varieties by the distinct coloring of its flowers, its vigorous growth habit, and its abundant production of flower stalks during the growing season; and the long-lasting quality of the blooming plant, as a cut flower, affords a commercial value believed to be at least as great as that of its commercially successful parent "Orchid." The primary distinction of the new variety over its parent resides in the over-all generally Yellow 13B–14A coloring of the flowers whereas the flowers of the parent plant have outer petals of a mainly White 155D color and only the inner petals are of the Yellow-Orange 17B color.

I claim:

1. The new and distinct variety of alstroemeria plant substantially as herein shown and described, characterized by the distinctive yellow color of its flowers, its abundant production of flowers during its twice annually blooming season, and the long lasting quality of the blooming plant as a cut flower.

No references cited.

ROBERT E. BAGWILL, Primary Examiner